United States Patent
Spector

(10) Patent No.: US 7,311,678 B2
(45) Date of Patent: *Dec. 25, 2007

(54) PRESSURE-PULSE THERAPY APPARATUS

(75) Inventor: Avner Spector, Savyon (IL)

(73) Assignee: Medispec Ltd., Yahud (IL)

( * ) Notice: Subject to any disclaimer, the term of this patent is extended or adjusted under 35 U.S.C. 154(b) by 108 days.

This patent is subject to a terminal disclaimer.

(21) Appl. No.: 10/617,037

(22) Filed: Jul. 11, 2003

(65) Prior Publication Data

US 2004/0010211 A1 Jan. 15, 2004

Related U.S. Application Data

(62) Division of application No. 09/814,359, filed on Mar. 22, 2001, now Pat. No. 6,755,796.

(51) Int. Cl.
*A61N 7/00* (2006.01)

(52) U.S. Cl. ............... 601/2; 601/4; 367/142; 367/147; 367/150; 367/151; 367/171; 367/174

(58) Field of Classification Search ........ 600/439; 601/2–4; 367/141, 142, 147, 150, 151, 171, 367/174, 175

See application file for complete search history.

(56) References Cited

U.S. PATENT DOCUMENTS

| | | | |
|---|---|---|---|
| 3,942,531 A | 3/1976 | Hoff et al. | |
| 4,570,634 A | 2/1986 | Wess | |
| 4,620,545 A | 11/1986 | Shene et al. | |
| 4,782,821 A | 11/1988 | Reitter | |
| 5,072,733 A | 12/1991 | Spector et al. | |
| 5,529,572 A | 6/1996 | Spector | |
| 5,873,845 A * | 2/1999 | Cline et al. | 601/3 |
| 5,904,659 A | 5/1999 | Duarte et al. | |
| 6,091,497 A | 7/2000 | Paritsky et al. | |
| 6,755,796 B2 * | 6/2004 | Spector | 601/2 |

FOREIGN PATENT DOCUMENTS

| | | |
|---|---|---|
| EP | 0369177 | 1/1997 |
| WO | WO 93/14720 | 8/1993 |

\* cited by examiner

*Primary Examiner*—Ruth S. Smith

(57) ABSTRACT

Disclosed is a device for producing an intracorporeal pressure pulse comprising a pressure pulse source configured to generate a collimated pressure pulse and an acoustic lens including at least one ring-shaped focusing section configured to focus a pressure pulse generated by the pressure pulse source substantially to the vicinity of the central axis of the ring-shaped focusing section.

20 Claims, 8 Drawing Sheets

ID# 7,311,678 B2

PRESSURE-PULSE THERAPY APPARATUS

RELATED APPLICATIONS

This is a Divisional Application of U.S. patent application Ser. No. 09/814,359, filed Mar. 22, 2001 issued as U.S. Pat. No. 6,755,796. This Application also claims priority from Israel Patent Application No. 141428, filed Feb. 14, 2001.

FIELD OF THE PRESENT INVENTION

The present invention relates generally to apparatus for pressure-pulse therapy. The present invention relates in particular to the generation of compound pressure pulses especially for orthopedic therapy.

BACKGROUND OF THE PRESENT INVENTION

Pressure-pulse therapy, also known as shock-wave therapy, has many uses It is used in lithotripsy as a noninvasive technique for pulverizing kidney stones and calculi in the bladder and urethra. It is also used for dissolving lipids in cells close to the skin and in the pelvic region. In particular, it has many uses in orthopedic medicine, for example, as a therapeutic means for any of the following:
i. osteoporosis and the inducement of bone growth;
ii. joining of bone fracture, especially, ununion fractures, i.e., fractures that have failed to unite and heal;
iii. disintegration of calculi and (or) calcification in fibers, joints, and tendinitis; and
iv. pain relief in the cases of calcific tendinitis of the shoulder joint, tennis elbow, golf elbow, and plantar fasciitis (with and, without heel spur).

U.S. Pat. No. 4,620,545 "Non-Invasive Destruction of Kidney Stones" to Shene et al, whose disclosure is incorporated herein by reference, describes a pressure-pulse therapy apparatus which includes an ellipsoidal reflector, having a first focal point within the reflector's dome and a second focal point outside the reflector's dome. A flexible diaphragm caps the reflector, and the region contained by the reflector and the diaphragm is filled with a liquid medium, for pulse propagation. A pressure-pulse source is located at the first focal point, within the medium. This configuration provides that a portion of a pulse originating from the source, at the first focal point, will impinge on the reflector, be reflected by it, and be brought into focus at the second focal point. The reflector is movable and can be positioned so that the second focal point coincides with a concretion within the body that is to be pulverized. Sonic aiming means are used to detect the concretion and to direct the positioning of the reflector.

In general, pressure-pulse therapy is accompanied by an imaging means, such as the sonic aiming means of U.S. Pat. No. 4,620,545. The region for treatment is generally small, between 0.3 and 1.5 cm, and it is desirous to image the location in order for the therapy to be applied effectively. X-ray imaging may be used; however, with x-rays, the patient and the physician are exposed to radiation doses with each treatment.

PCT patent publication PCT WO 93/14720, "Method and Apparatus Particularly Useful for Treating Osteoporosis," to Spector, whose disclosure is incorporated herein by reference, offers an alternative to the need for an imaging means. It has a generally parabolic reflector, which has a single focal point within the reflector's dome. A flexible diaphragm caps the reflector and the region contained by the reflector and the diaphragm is filled with a liquid medium, as in the previous patent. A pressure-pulse source is located at the focal point, within the liquid. This configuration provides that a portion of a pulse originating from the source, at the focal point, will impinge on the reflector, and be reflected by it, collimated. In other words, the reflected pulse will be a non-focusing wave, so focusing means are not essential. Pressure pulse therapy can thus be image free.

However, with a collimated beam, some pressure pulse energy is lost, when compared with a beam that is focused at the region for treatment. It would be desirable to direct more of the pressure-pulse energy at the region for treatment, without being dependent on an imaging means.

SUMMARY OF THE PRESENT INVENTION

The present invention seeks to provide a therapeutic pressure pulse formed as a compound pressure pulse of at least two subordinate pulses.

There is thus provided, in accordance with the present invention a dome-shaped reflector, having:
a center section, having predetermined first curvature and reflective characteristics associated therewith, and formed to reflect a primary pressure pulse propagating thereon, so as to form a first subordinate pressure pulse of a compound pressure pulse and
at least one ring section, substantially concentric with said center section, having predetermined second curvature and reflective characteristics associated therewith, and formed to reflect the primary pressure pulse propagating thereon, so as to form at least one additional subordinate pressure pulse of said compound pressure pulse.

Additionally, in accordance with the present invention, said center section is substantially parabolic and has a single focal point.

Further in accordance with the present invention, said at least one ring section is substantially ellipsoid and has proximal and distal focal points with respect to said reflector, wherein said focal point of said center section and said proximal focal point of said at least one ring section substantially coincide.

Additionally, in accordance with the present invention, said at least one ring section includes a plurality of substantially ellipsoid ring sections, each having proximal and distal focal points with respect to said reflector, wherein said proximal focal points of said plurality of ring sections substantially coincide, wherein said distal focal points of said plurality of ring sections are adjacent to each other, and wherein said focal point of said center section and said proximal focal points of said plurality of ring sections substantially coincide.

Alternatively, said center section and said at least one ring section are substantially ellipsoid, each having proximal and distal focal points with respect to said reflector, wherein said proximal focal point of said center section and said proximal focal point of said at least one ring section substantially coincide.

Alternatively, said center section is generally parabolic and has a single focal zone.

Additionally, said at least one ring section is generally ellipsoid, and has proximal and distal focal zones with respect to said reflector, wherein said focal zone of said center section and said proximal focal zone of said at least one ring section generally coincide.

Additionally, said at least one ring section includes a plurality of generally ellipsoid ring sections, each having proximal and distal focal zones with respect to said reflector, wherein said proximal focal zones of said plurality of ring sections generally coincide, wherein said distal focal zones of said plurality of ring sections are generally adjacent to each other, and wherein said focal zone of said center section and said proximal focal zones of said plurality of ring sections generally coincide.

Alternatively, said center section and said at least one ring section are generally ellipsoid, each having proximal and distal focal zones with respect to said reflector, wherein said proximal focal zone of said center section and said proximal focal zone of said at least one ring section generally coincide.

Alternatively, said predetermined curvatures and reflective characteristics are determined by numerical analysis.

Additionally, said predetermined curvatures and reflective characteristics include a predetermined zone at which both said first subordinate pressure pulse and said at least one additional subordinate pressure pulse are reflected.

Alternatively, said predetermined curvatures and reflective characteristics include:
  a predetermined point at which said first subordinate pressure pulse is reflected; and
  a predetermined point at which said at least one additional subordinate pressure pulse is reflected.

Alternatively, said predetermined curvatures and reflective characteristics include:
  a predetermined zone at which said first subordinate pressure pulse is reflected; and
  a predetermined zone at which said at least one additional subordinate pressure pulse is reflected.

Alternatively, said predetermined first curvature is selected from a group which consists of generally parabolic, generally ellipsoid, substantially ellipsoid, and a curvature which is determined by numerical analysis to yield said predetermined first reflective characteristics.

Additionally, said predetermined second curvature is selected from a group which consists of generally parabolic, substantially parabolic, generally ellipsoid, substantially ellipsoid, and a curvature which is determined by numerical analysis to yield said predetermined second reflective characteristics.

Further in accordance with the present invention, said predetermined curvature and reflective characteristics include a predetermined phase difference between said first subordinate pressure pulse and said at least one additional subordinate pressure pulse.

Additionally, in accordance with the present invention, said phase difference is between 0.5 and 1 microsecond.

Additionally, in accordance with the present invention, said at least one ring section, having predetermined second curvature and reflective characteristics associated therewith, includes a plurality of ring sections, each having predetermined curvature and reflective characteristics associated therewith, formed to reflect a primary pressure pulse propagating thereon, from said pressure-pulse source, so as to form a plurality of additional subordinate pressure pulses of the compound pulse, wherein said plurality of additional subordinate pressure pulses of the compound pulse include predetermined phase differences between them.

There is thus also provided, in accordance with the present invention, a dome-shaped reflector, having:
  a center section, having predetermined first curvature and reflective characteristics associated therewith, and formed to reflect a primary pressure pulse propagating thereon, so as to form a first subordinate pressure pulse of a compound pressure pulse; and
  at least one ring section, generally concentric with said center section, having predetermined second curvature and reflective characteristics associated therewith, and formed to reflect the primary pressure pulse propagating thereon, so as to form at least one additional subordinate pressure pulse of said compound pressure pulse.

There is thus also provided, in accordance with the present invention, pressure-pulse therapy apparatus, which includes:
  a dome-shaped reflector, having:
    a center section, having predetermined first curvature and reflective characteristics associated therewith, and formed to reflect a primary pressure pulse propagating thereon, so as to form a first subordinate pressure pulse of a compound pressure pulse; and
    at least one ring section, substantially concentric with said center section, having predetermined second curvature and reflective characteristics associated therewith, and formed to reflect the primary pressure pulse propagating thereon, so as to form at least one additional subordinate pressure pulse of said compound pressure pulse;
  an x-axis passing through its center;
  an open end;
  a flexible diaphragm, which caps said open end;
  a fluid medium contained within said reflector and said diaphragm, for facilitating propagation of the pressure pulses;
  a pressure-pulse source, immersed in said medium, located between said reflector and said diaphragm, on said x-axis, for generating the primary pressure pulse; and
  a power supply, which supplies power to said pressure-pulse source.

Additionally, in accordance with the present invention, said first and second curvatures and reflective characteristics are associated with a point P, located on said x-axis, wherein said pressure-pulse source is located at said point P.

Alternatively, said first and second curvatures and reflective characteristics are associated with a point P, located on said x-axis, wherein said pressure-pulse source is located at a point P" on said x-axis.

Additionally, said point P is more proximal to said reflector than said point P".

Alternatively, said point P is more distal to said reflector than said point P".

Further in accordance with the present invention, said apparatus includes a linear extender for varying a distance between said pressure-pulse source and said reflector, alone said x-axis.

Additionally, in accordance with the present invention, said pressure-pulse source is selected from a group which consists of substantially and generally point pressure-pulse sources.

Further in accordance with the present invention, said pressure-pulse source is a spark discharge source.

Alternatively, said pressure-pulse source is an electromagnetic pressure-pulse source.

Additionally, in accordance with the present invention, said pressure-pulse is operable to generate primary pressure pulses in the range between 1000 and 6000 bars.

Further in accordance with the present invention, said apparatus is operable to generate, from the primary pressure pulse, subordinate pressure pulses in the range between 5 and 600 bars.

Additionally, in accordance With the present invention, said apparatus is arranged for traveling along at least one axis, for positioning against a tissue surface of a body.

Further in accordance with the present invention, said apparatus is arranged for traveling along a plurality of axes, for positioning against a tissue surface of a body.

Additionally, in accordance with the present invention, said apparatus is arranged for tilting along at least one angular direction, for positioning against a tissue surface of a body.

Further in accordance with the present invention, said apparatus is arranged for tilting along a plurality of angular directions, for positioning against a tissue surface of a body.

Additionally, in accordance with the present invention, said apparatus includes a support fixture for a portion of a body to be treated.

There is thus also provided, in accordance with the present invention, pressure-pulse therapy apparatus, which includes:
  a dome-shaped reflector, having:
    a center section, having predetermined first curvature and reflective characteristics associated therewith, and formed to reflect a primary pressure pulse propagating thereon, so as to form a first subordinate pressure pulse of a compound pressure pulse; and
    at least one ring section, generally concentric with said center section, having predetermined second curvature and reflective characteristics associated therewith, and formed to reflect the primary pressure pulse propagating thereon, so as to form at least one additional subordinate pressure pulse of said compound pressure pulse;
  an x-axis passing through its center;
  an open end;
  a flexible diaphragm, which caps said open end;
  a fluid medium contained within said reflector and said diaphragm, for facilitating propagation of the pressure pulses;
  a pressure-pulse source, immersed in said medium, located between said reflector and said diaphragm, on said x-axis, for generating the primary pressure pulse; and
  a power supply, which supplies power to said pressure-pulse source.

There is thus also provided, in accordance with the present invention, a pressure-pulse therapy method, which includes:
  generating a primary pressure-pulse;
  propagating the primary pressure pulse in a fluid medium, employing a reflector, having:
    a center section, having first curvature and reflective characteristics associated therewith; and
    at least one ring section, having second curvature and reflective characteristics associated therewith;
  reflecting a first portion of the primary pressure pulse by the center section, thus forming a first subordinate pressure pulse of a compound pressure pulse; and
  reflecting at least one additional portion of the primary pressure pulse by the at least one ring section, thus forming at least one additional subordinate pressure pulse of said compound pressure pulse.

Additionally, in accordance with the present invention, reflecting a first portion of the propagation includes reflecting the propagation in a substantially collimated manner.

Alternatively, reflecting a first portion of the propagation includes reflecting the propagation in a generally collimated manner.

Alternatively, reflecting a first portion of the propagation includes reflecting the propagation as a substantially focusing propagation.

Alternatively, reflecting a first portion of the propagation includes reflecting the propagation as a generally focusing propagation.

Additionally, in accordance with the present invention, reflecting at least one additional portion of the propagation includes reflecting the propagation as a substantially focusing propagation.

Alternatively, reflecting at least one additional portion of the propagation includes reflecting the propagation as a generally focusing propagation.

Additionally, in accordance with the present invention, said method includes reflecting the first portion of the primary pressure pulse propagation and reflecting at least one additional portion of the primary pressure pulse propagation with a phase difference between them.

Further in accordance with the present invention, employing a reflector includes employing a reflector formed of a plurality of sections that include:
  a center section, having predetermined first curvature and reflective characteristics associated therewith; and
  a plurality of ring sections, having predetermined curvatures and reflective characteristics associated therewith,
  wherein reflecting at least one additional portion of the primary pressure pulse propagation includes reflecting a plurality of additional portions of the primary pressure pulse propagation by said plurality of sections, thus forming a plurality of additional subordinate pressure pulses.

Additionally, in accordance with the present invention, said method includes reflecting the plurality of additional portions of the primary pressure pulse propagation with phase differences between them.

Further in accordance with the present invention, said method includes varying a distance between the reflector and a pressure-pulse source.

Additionally, in accordance with the present invention, said method includes therapeutically applying the compound pressure pulse to a tissue of a body.

Further in accordance with the present invention, the tissue is human tissue.

There is thus also provided, in accordance with the present invention, a disk-like acoustic lens, having:
  a center section, having predetermined first curvature and focusing characteristics associated therewith, and formed to direct a primary pressure pulse propagating thereon, so as to form a first subordinate pressure pulse of a compound pressure pulse; and
  at least one ring section, substantially concentric with said center section, having predetermined second curvature and focusing characteristics associated therewith, and formed to direct the primary pressure pulse propagating thereon, so as to form at least one additional subordinate pressure pulse of said compound pressure pulse.

Additionally, in accordance with the present invention, said predetermined curvatures and focusing characteristics are determined by numerical analysis.

Further in accordance with the present invention, said predetermined curvatures and focusing characteristics include a predetermined zone at which both said first subordinate pressure pulse and said at least one additional subordinate pressure pulse are directed.

Alternatively, said predetermined curvatures and focusing characteristics include:

a predetermined point at which said first subordinate pressure pulse is directed; and a predetermined point at which said at least one additional subordinate pressure pulse is directed.

Alternatively, said predetermined curvatures and focusing characteristics include:

a predetermined zone at which said first subordinate pressure pulse is directed; and a predetermined zone at which said at least one additional subordinate pressure pulse is directed.

Alternatively, said predetermined curvatures and focusing characteristics include a predetermined phase difference between said first subordinate pressure pulse and said at least one additional subordinate pressure pulse.

Additionally, in accordance with the present invention, said phase difference is between 0.5 and 1 microsecond.

Further, in accordance with the present invention, said at least one ring section, having predetermined second curvature and focusing characteristics associated therewith, includes a plurality of ring sections, each having predetermined curvatures and focusing characteristics associated therewith, formed to reflect a primary pressure pulse propagating thereon, so as to form a plurality of additional subordinate pressure pulses of said compound pressure pulse.

Additionally, in accordance with the present invention, said plurality of additional subordinate pressure pulses of said compound pressure pulse include predetermined phase differences between them.

Additionally, in accordance with the present invention, said lens includes a cutout section that allows a portion of the primary pressure pulse to pass through it, undisturbed.

Additionally, in accordance with the present invention, said cutout section is said center section.

There is thus also provided, in accordance with the present invention, a disk-like acoustic lens, having:

a center section, having predetermined first curvature and focusing characteristics associated therewith, and formed to direct a primary pressure pulse propagating thereon, so as to form a first subordinate pressure pulse of a compound pressure pulse; and at least one ring section, generally concentric with said center section, having predetermined second curvature and focusing characteristics associated therewith, and formed to direct the primary pressure pulse propagating thereon, so as to form at least one additional subordinate pressure pulse of said compound pressure pulse.

There is thus also provided, in accordance with the present invention, pressure-pulse therapy apparatus, which includes:

a disk-like acoustic lens, having:
a center section, having predetermined first curvature and focusing characteristics associated therewith, and formed to direct a primary pressure pulse propagating thereon, so as to form a first subordinate pressure pulse of a compound pressure pulse; and at least one ring section, substantially concentric with said center section, having predetermined second curvature and focusing characteristics associated therewith, and formed to direct a primary pressure pulse propagating thereon, so as to form at least one additional subordinate pressure pulse of said compound pressure pulse;

proximal and distal sides with respect to a tissue for treatment;

an enclosure with an open end;

a flexible diaphragm, which caps said open end;

a fluid medium, contained within said enclosure, for facilitating propagation of the pressure pulses;

a pressure-pulse source, which includes a disk-like, electromagnetic pressure-pulse source, immersed in the medium, located at said distal side of said acoustic lens, for generating a collimated primary pressure pulse that propagates in said medium, and impinges on said acoustic lens; and a power supply, which supplies power to said pressure-pulse source.

There is thus also provided, in accordance with the present invention, pressure-pulse therapy apparatus, which includes:

a disk-like acoustic lens, having:
a center section, having predetermined first curvature and focusing characteristics associated therewith, and formed to direct a primary pressure pulse propagating thereon, so as to form a first subordinate pressure pulse of a compound pressure pulse; and at least one ring section, generally concentric with said center section, having predetermined second curvature and focusing characteristics associated therewith, and formed to direct a primary pressure pulse propagating thereon, so as to form at least one additional subordinate pressure pulse of said compound pressure pulse;

proximal and distal sides with respect to a tissue for treatment;

an enclosure with an open end;

a flexible diaphragm, which caps said open end;

a fluid medium, contained within said enclosure, for facilitating propagation of the pressure pulses;

a pressure-pulse source, which includes a disk-like, electromagnetic pressure-pulse source, immersed in the medium, located at said distal side of said acoustic lens, for generating a collimated primary pressure pulse that propagates in said medium, and impinges on said acoustic lens; and a power supply, which supplies power to said pressure-pulse source.

There is thus also provided, in accordance with the present invention, a pressure-pulse therapy method, which includes:

generating a primary pressure pulse;

propagating the primary pressure pulse in a fluid medium;

employing a disk-like acoustic lens, formed of at least two sections, which include:
a center section, having predetermined first curvature and focusing characteristics associated therewith; and at least one ring section, having predetermined second curvature and focusing characteristics associated therewith;

focusing a first portion of the primary pressure pulse by the center section, thus forming a first subordinate pressure pulse of a compound pressure pulse; and focusing at least one additional portion of the primary pressure pulse by the at least one additional ring section, thus forming at least one additional subordinate pressure pulse of said compound pressure pulse.

Additionally, in accordance with the present invention, focusing a first portion of the propagation includes substantially focusing the propagation.

Alternatively, focusing a first portion of the propagation includes generally focusing the propagation.

Additionally, in accordance with the present invention, focusing at least one additional portion of the propagation includes substantially focusing the propagation.

Alternatively, focusing at least one additional portion of the propagation includes, generally focusing the propagation.

Additionally, in accordance with the present invention, focusing the first portion of the primary pressure pulse propagation and focusing at least one additional portion of the primary pressure pulse propagation with a phase difference between them.

Further in accordance with the present invention, employing a lens formed of at least two sections includes employing a lens formed of a plurality of sections, having predetermined curvatures and focusing characteristics associated therewith, wherein focusing at least one additional portion of the primary pressure pulse propagation includes focusing a plurality of additional portions of the primary pressure pulse propagation by said plurality of sections, thus forming a plurality of additional subordinate pressure pulses.

Additionally, in accordance with the present invention, said plurality of additional subordinate pressure pulses include predetermined phase differences between them.

BRIEF DESCRIPTION OF THE DRAWINGS

The present invention will be more clearly understood from the accompanying detailed description and drawings, in which same number designations are maintained throughout the figures for each element and in which.

DETAILED DESCRIPTION OF PREFERRED EMBODIMENTS

Figure 1:
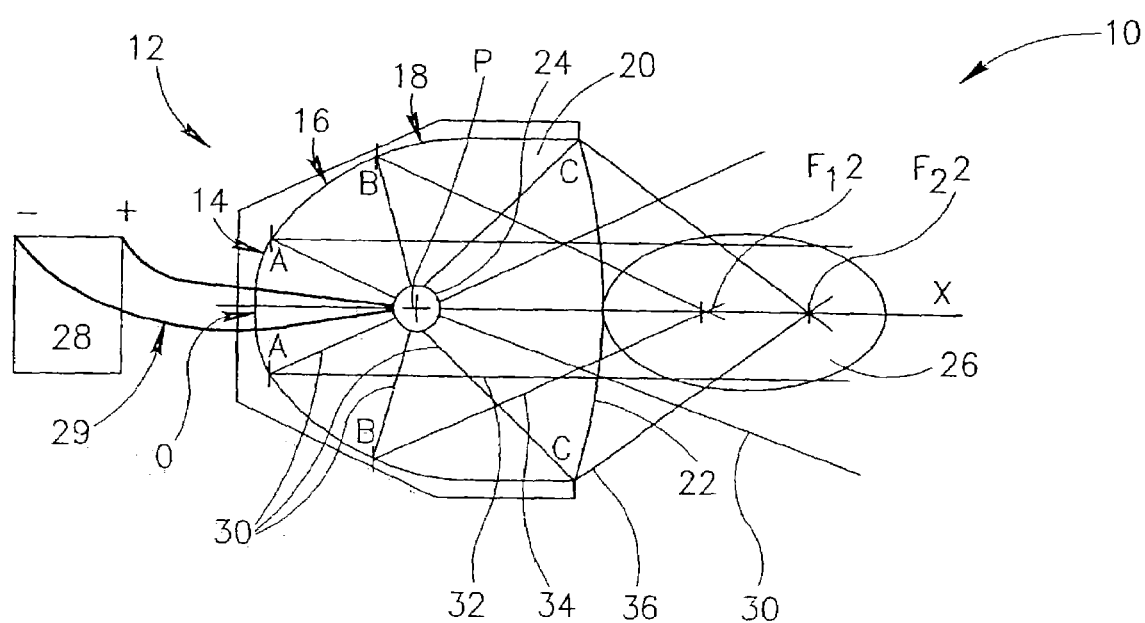
FIG. 1 is a schematic representation of pressure-pulse therapy apparatus, in accordance with a preferred embodiment of the present invention.

Reference is now made to FIG. 1, which schematically illustrates pressure-pulse therapy apparatus 10, in accordance with a preferred embodiment of the present invention. Pressure-pulse apparatus 10 includes a dome-shaped reflector 12, defining an x-axis passing through its center, and a point of origin O at its center (vertex). Reflector 12 is formed of three substantially concentric sections having different curvatures: a substantially parabolic center section 14, a substantially ellipsoid ring section 16, and a second substantially ellipsoid ring section 18.

Figure 2A:
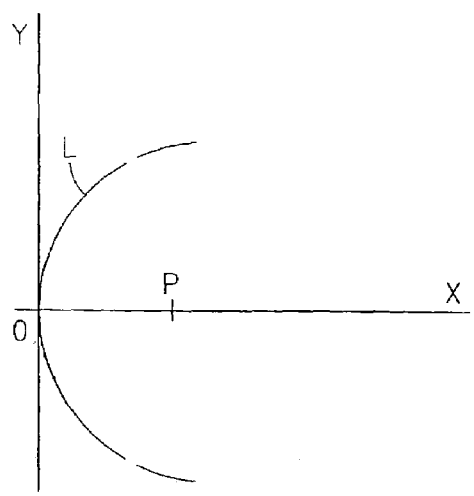
FIG. 2A is a schematic representation of a parabola.
Figure 2B:
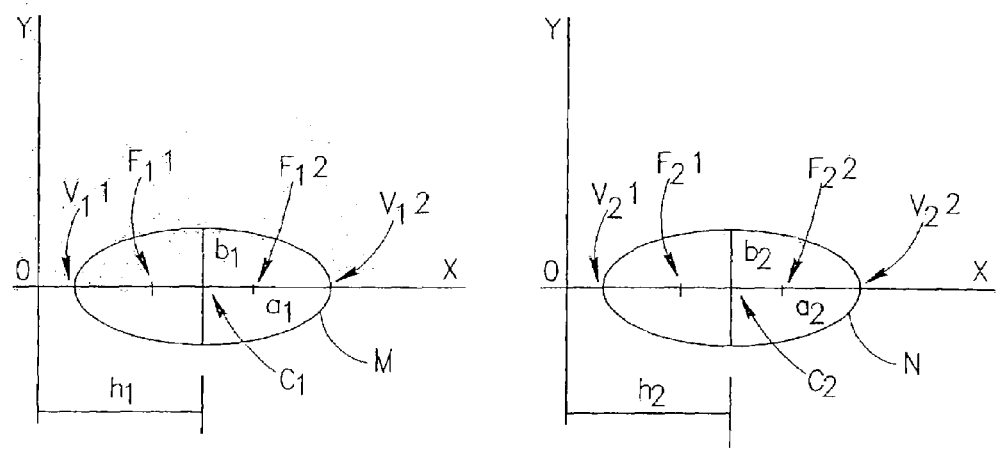
FIG. 2B is a schematic representation of ellipses.

In order to illustrate the implications of this particular geometry, reference is now made to FIGS. 2A and 2B, for a basic review of the important features of a parabola and an ellipse, as they relate to the present invention. The following discussion is based on "Standard Mathematical Tables," Editor-in-Chief of Mathematics S. M. Selby, The Chemical Rubber Co. (CRC), Eighteenth Edition, pp. 355-356.

FIG. 2A schematically illustrates an x-y coordinate system with point of origin O, and a parabola, L, whose vertex, V coincides with point O, and whose mathematical expression is given by:

$$y^2 = \pm 4Px. \qquad 1.$$

The focal point, F, of parabola L is at (P,0).

FIG. 2B schematically illustrates the x-y coordinate system with point of origin O, and two ellipses, M and N.

Generally, an ellipse has two vertices, V1 and V2, major and minor axes, a and b, and a center C. The mathematical expression describing an ellipse with a center located on the x-axis, at some point (h,0) is:

$$(x-h)^2/a^2 + y^2/b^2 = 1. \qquad 2.$$

wherein, when center C coincides with point of origin O, the mathematical expression of the ellipse is $x^2/a^2 + y^2/b^2 = 1$.

The ellipse has two focal points, F1 and F2, and the distance from the center to either focal point is given by:

$$\pm(a^2-b^2)^{1/2}. \qquad 3.$$

Therefore, F1 is at:

$$F1 = h - (a^2-b^2)^{1/2}. \qquad 4.$$

while F2 is at:

$$F2 = h + (a^2-b^2)^{1/2}. \qquad 5.$$

Figure 3:
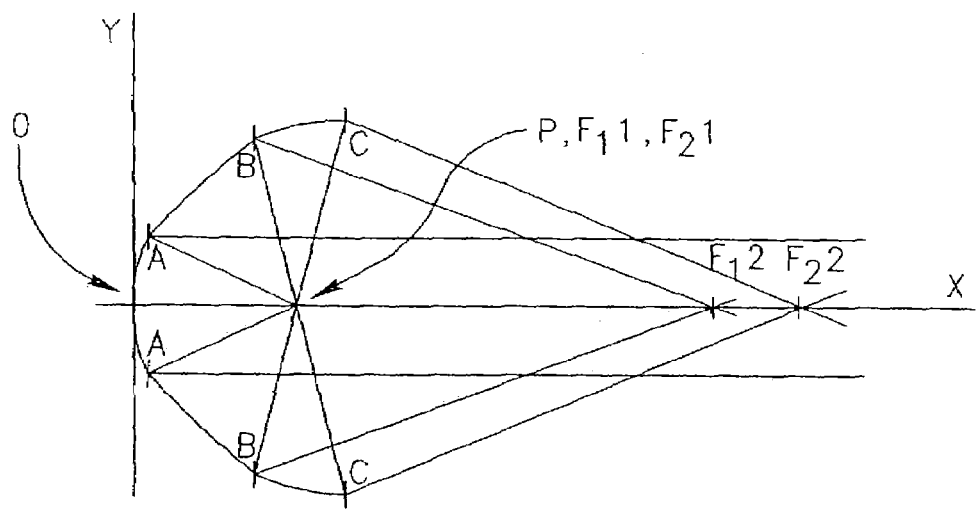
FIG. 3 is a schematic representation of the specific geometry of a reflector formed of three substantially concentric sections, in accordance with a preferred embodiment of the present invention.

Reference is now also made to FIG. 3, which schematically illustrates the special geometry of reflector 12 of FIG. 1. Preferably, a center section, between point O and points A-A is a section of parabola L, with vertex, V, at point O and a curvature described by expression 1 above. The focal point of this section, F, is at (P,0), or, $$F=P. \qquad 6.$$

Preferably, a first ring section, between points A-A and B-B, is a section of ellipse M, having a curvature described by the expression:

$$(x-h_1)^2/a_1^2 + y^2/b_1^2 = 1. \qquad 7.$$

Thus, a first, or proximal focal point, with respect to the reflector is at:

$$F_1 1 = h_1 - (a_1^2 - b_1^2)^{1/2}, \qquad 8.$$

and a second, or distal focal point, with respect to the reflector is at:

$$F_12=h_1+(a_1^2-b_1^2)^{1/2}. \qquad 9.$$

In a similar manner, a second ring section, between points B-B and C-C, is a section of ellipse N, having a curvature described by the expression:

$$(x-h_2)^2/a_2^2+y^2/b_2^2=1. \qquad 10.$$

Its proximal focal point, with respect to the reflector is at:

$$F_21=h_2-(a_2^2-b_2^2)^{1/2}, \qquad 11.$$

and its distal focal point, with respect to the reflector is at:

$$F_22=h_2+(a_2^2-b_2^2)^{1/2}. \qquad 12.$$

A condition of a preferred embodiment of the present invention, as described in FIG. 3, is that the focal point of the center, parabolic section, F, and the proximal focal points of the ellipsoid ring sections $F_1 1$ and $F_2 1$ coincide, or:

$$P=F=F_1 1=F_2 1 \qquad 13.$$

and $$P=F=h_1-(a_1^2-b_1^2)^{1/2}=h_2-(a_2^2-b_2^2)^{1/2}. \qquad 14.$$

Where still additional ellipsoid ring-sections are used, the two conditions are extended to the additional rings. When the center section is also ellipsoid, the proximal focal points of all the ellipsoid sections should coincide.

Preferably, the distal focal points $F_1 2$ and $F_2 2$ of the two ellipsoid ring sections, are different from each other, $$F_1 2 \neq F_2 2, \qquad 15.$$

and, $$h_1+(a_1^2-b_1^2)^{1/2} \neq h_2+(a_2^2-b_2^2)^{1/2}, \qquad 16.$$

and similarly, for additional ellipsoid ring sections, when they are used.

Preferably, along ring A-A, the y values and preferably also the first derivatives dy/dx of the center, parabolic section and of the first ellipsoid ring section are substantially the same, and preferably, along ring B-B, the y values and preferably also the first derivatives dy/dx of the first and the second ellipsoid ring sections are substantially the same, so as to avoid points of discontinuities which may cause pressure losses. However this condition is not required for the present invention.

Reference is again made to FIG. 1, where in accordance with a preferred embodiment, the curvature of section 14 is substantially described by expression 1, the curvature of section 16 is substantially described by expression 7, and the curvature of section 18 is substantially described by expression 10. Preferably, the values of P, $h_1$, $a_1$, $b_1$, $h_2$, $a_2$, and $b_2$ are selected in a manner that meets the conditions specified by expressions 13-16. Thus, focal point F of substantially parabolic center section 14 and proximal focal points $F_1 1$ and $F_2 1$ of substantially ellipsoid ring sections 16 and 18 coincide at a point P, on the x axis, preferably inside dome-shaped reflector 12. Distal focal point $F_1 2$ of section 16 and distal focal point $F_2 2$ of section 18 are at different distances from reflector 12, on the x axis, preferably within a region for treatment 26 of body tissue. In some preferred embodiments, the parameters of sections 14, 16, and 18, namely, P, $h_1$, $a_1$, $b_1$, $h_2$, $a_2$, and $b_2$ are selected in a manner that provides for each first derivative along rings A, B, and C, to have a single value, when calculated from the left and when calculated from the right. In this way, pressure losses due to points of discontinuities will be reduced. In some preferred embodiments, $h_1=a_1$, and substantially ellipsoid ring section 16 is constructed as if its first vertex were at point of origin O. Alternatively or additionally, $h_2=a_2$. In some preferred embodiment of the present invention, sample values for the aforementioned parameters are as follows, P=30; $h_1$=30; $a_1$=65; $b_1$=25; $h_2$=35; $a_2$=70 $b_2$=27.

A pressure-pulse source 24 is located at point P. Source 24 and reflector 12 are arranged in a fluid medium 20, preferably a liquid, such as an aqueous solution, water or oil, in which the pressure pulses propagate. A flexible diaphragm 22 essentially caps dome-shaped reflector 12 and contains fluid medium 20 within. When conducting therapeutic treatment, flexible diaphragm 22 of apparatus 10 is pressed against region for treatment 26, so that pressure pulses propagate through diaphragm 22 to region for treatment 26.

Preferably, pressure-pulse source 94 is a substantially point source. Alternatively, pressure-pulse source 24 is a generally point source. Pressure pulse source 24 may be, for example, a spark discharge source described in U.S. Pat. No. 3,942,531 to Hoff, 1976, whose disclosure is incorporated herein by reference. Alternatively, any spark plug source, electromagnetic source, piezoelectric source, or another known source may be used.

A power supply unit 28, preferably located outside medium 20, powers pressure-pulse source 24, with wires 29 connecting power supply unit 28 to source 24.

The configuration of FIG. 1 provides for a radially expanding primary pulse 30, originating from substantially or generally point source 24, to form a compound of subordinate pulses, as follows:

i. a first subordinate pulse 32, being a substantially collimated pulse, reflected from substantially parabolic center section 14;

ii. a second subordinate pulse 34, being a substantially focusing pulse, reflected from substantially ellipsoid ring section 16, toward distal focal point $F_1 2$, preferably, within region for treatment 26; and iii a third subordinate pulse 36, being a substantially focusing pulse, reflected from substantially ellipsoid ring section 18, toward distal focal point $F_2 2$, preferably, within region for treatment 26.

Additionally, a portion of radially expanding primary pulse 30 will impinge on region for treatment 26, reaching it even before first subordinate pulse 32.

Figure 4:
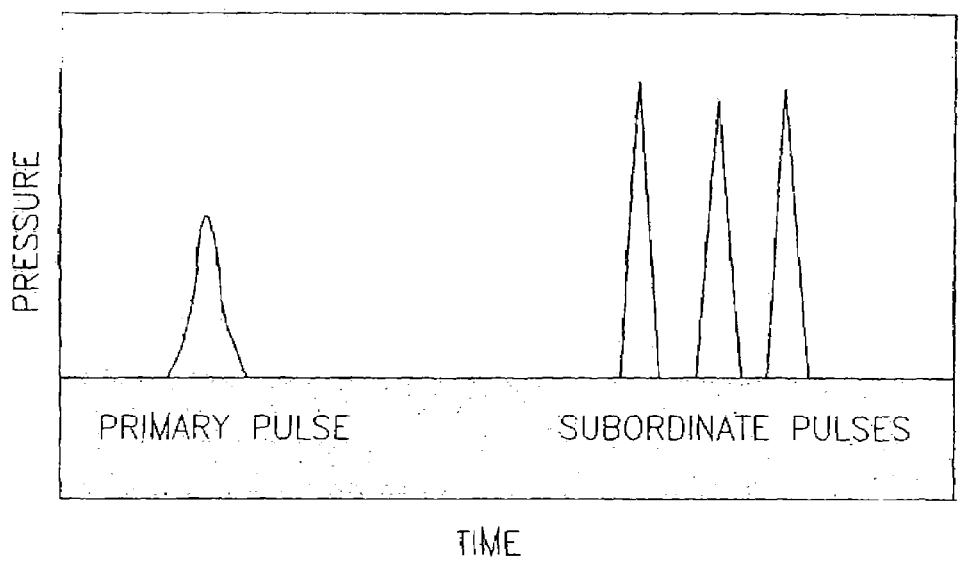
FIG. 4 is a schematic representation of a compound pressure pulse formed of subordinate pulses, as a function of time, in accordance with a preferred embodiment of the present invention.

Reference is now made to FIG. 4, which schematically illustrates the effect of primary pressure pulse 30 on region for treatment 26, as a function of time. A portion of radially expanding primary pulse 30 is the first to impinge on region for treatment 26. However, because of the radial nature of the expansion, its amplitude will be relatively low. Subordinate pulses 32, 34, and 36, reflected from reflector 12, will impinge on region for treatment 26 a little later, generally at different times, since the paths are different for each subordinate pulse.

Radially expanding portion of primary pressure pulse 30 and collimated first subordinate pulse 32 inherently provide for regional treatment of the tissue. The combined effect of second subordinate pulse 34 and third subordinate pulse 36, each being directed at a different focal point within region for treatment 26, enhances the regional effect of the treatment.

In some preferred embodiments, only one substantially ellipsoid ring section, such as substantially ellipsoid ring section 16 is used, and the compound pressure pulse that is formed has only two subordinate pulses. Alternatively, more than two substantially ellipsoid ring sections are used, and the compound pressure pulse that is formed has three or more subordinate pulses.

Figure 5:
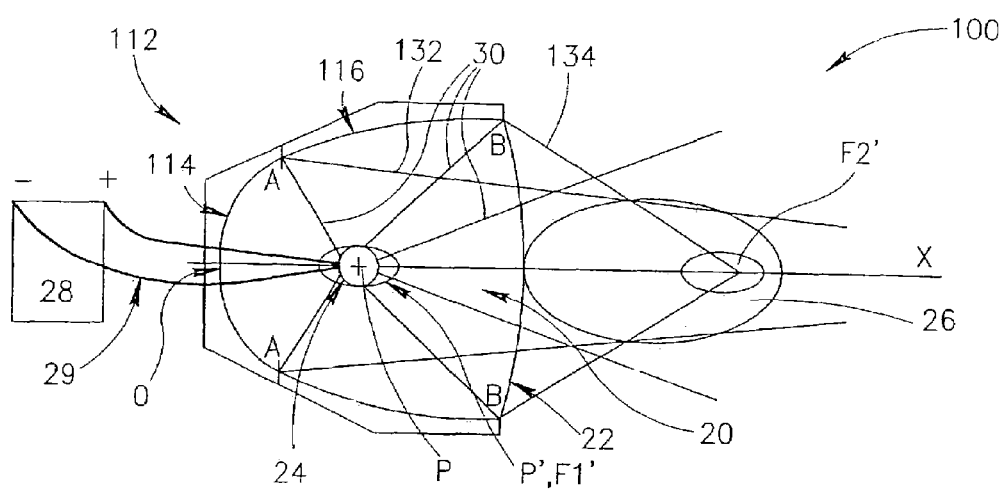
FIG. 5 is a schematic representation of pressure-pulse therapy apparatus, in accordance with a second embodiment of the present invention.

Reference is now made to FIG. 5, which schematically illustrates pressure-pulse therapy apparatus 100, in accordance with a second embodiment of the present invention. Pressure-pulse therapy apparatus 100 includes a generally, but not exactly, parabolic center section 114, having a focal zone P', generally around point P. Focal zone P' can be determined as follows: a collimated propagation impinging on generally parabolic center section 114 will be directed as focal zone P', thus defining focal zone P'. Preferably, focal zone P' is within the reflector's dome.

Preferably, pressure-pulse therapy apparatus 100 further includes a generally, but not exactly, ellipsoid ring section 116, having a proximal focal zone F1', which generally coincides with P', and a distal focal zone F2', preferably within region for treatment 26. Focal zone F2' can be determined as follows: a radially expanding propagation, originating from substantially or generally point source 24 at a point in the center of focal zone F1' and impinging on generally ellipsoid ring section 116, will be directed at focal zone F2', thus defining focal zone F2'. Similarly, focal zone F1' can be determined as follows: a radially expanding propagation, originating from a substantially or generally point source (not shown) at a point in the center of focal zone F2' and impinging on generally ellipsoid ring section 116, will be directed at focal zone F1', thus defining focal zone F1'.

Preferably, when a portion of primary pulse 30 impinges on generally parabolic center 114, it is reflected as a slightly convergent or slightly divergent first subordinate pulse 132.

Preferably, when a portion of primary pulse 30 impinges on generally ellipsoid ring 116, it is reflected as a poorly focusing second subordinate pulse 134, generally directed at zone F2', preferably within region for treatment 26, rather than at a point such as $F_1 2$ of FIG. 1. In this manner, regional treatment is rendered also by subordinate pulse 134, reflected from a single, generally ellipsoid ring section.

Figure 6:
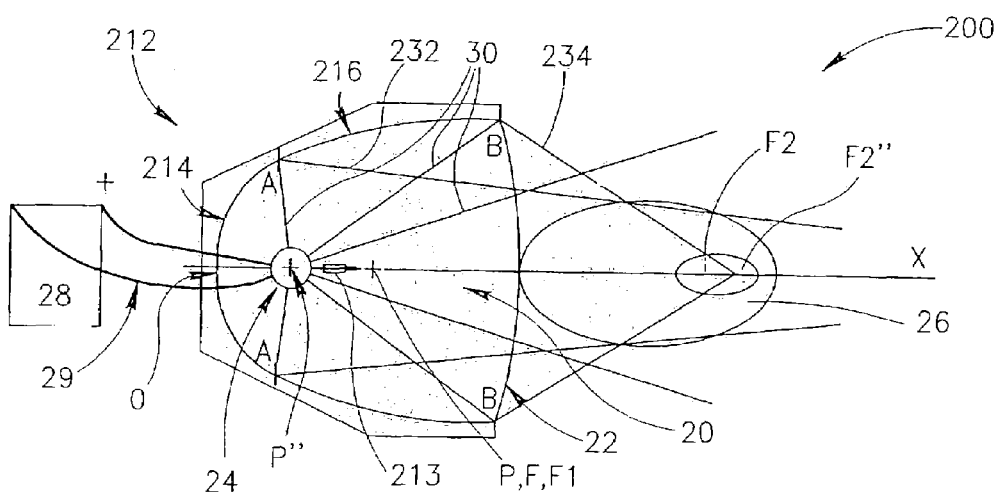
FIG. 6 is a schematic representation of pressure-pulse therapy apparatus, in accordance with a third embodiment of the present invention.

Reference is now made to FIG. 6, which is a schematic representation of pressure-pulse therapy apparatus 200, in accordance with a third embodiment of the present invention. Pressure-pulse therapy apparatus 200 includes a dome-shaped reflector 212 formed of two substantially concentric sections having different curvatures: a substantially parabolic center section 214 having a focal point F at point P, and a substantially ellipsoid ring section 216 having a proximal focal point F1, at point P, and a distal focal point F2. Pressure-pulse source 24 is located on the x-axis, at a point P''', preferably, somewhat closer to reflector 212 than point P. This configuration also provides that a radially expanding primary pulse 30, originating from pressure-pulse source 24 will impinge on reflector 212 and be reflected by it as a compound pressure pulse of somewhat diffused subordinate pulses: a first subordinate pulse 232 which will be slightly convergent, and a poorly focusing second subordinate pulse 234, generally directed at a zone F2'', preferably within region for treatment 26. This configuration, too, provides for a regional treatment of the tissue.

Alternatively, point P''', at which pressure-pulse source 24 is located, is further away from reflector 212 than point P.

Alternatively or additionally, pressure-pulse therapy apparatus 200 includes a linear extendor 213 for varying a distance between pressure-pulse source 24 and reflector 212, along, said x-axis, so as to selectably bring point P''' to coincidence with point P, when desired, to selectably bring point P''' to the right of point P, when desired, and to selectably bring point P''' to the left of point P, when desired.

Alternatively or additionally, reflector 212 is arranged for traveling along the x-axis, with respect to pressure-pulse source 24, so as to selectably bring point P''' to coincidence with point P, when desired, to selectably bring point P''' to the right of point P, when desired, and to selectably bring point P''' to the left of point P, when desired.

Preferably, traveling along the x-axis includes sliding on a rail or in a channel. Alternatively, travelling along the x-axis includes travelling on a threaded rod. Alternatively, another travelling mechanism may be used.

In some preferred embodiments, center region 14 is also substantially ellipsoid.

In some preferred embodiments, functions other than a parabola and an ellipse and different combinations of functions may be used for the curvature of the substantially concentric sections of the reflector. For example, a linear function may be used.

Figure 7:
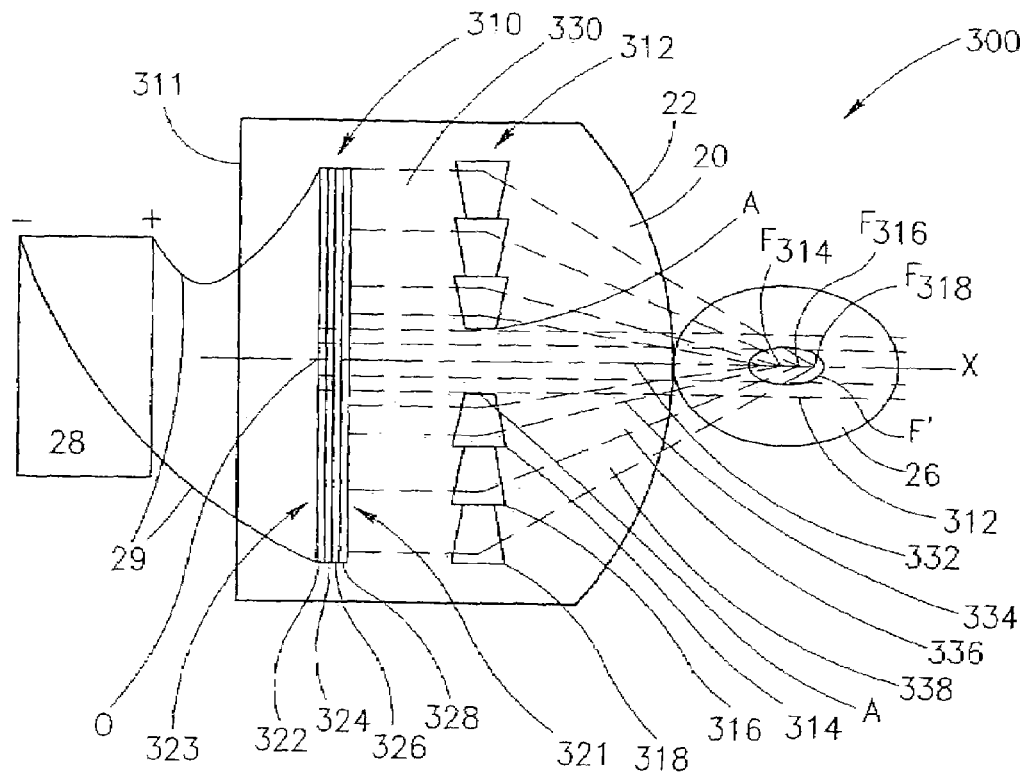
FIG. 7 is a schematic representation of pressure-pulse therapy apparatus, in accordance with a fourth embodiment of the present invention.

Reference is now made to FIG. 7, which is a schematic representation of pressure-pulse therapy apparatus 300, in accordance with a fourth embodiment of the present invention. Pressure-pulse apparatus 300 includes an electromagnetic source 310, for example, of a type described in U.S. Pat. No. 4,782,821, to Reitter, incorporated herein by reference. Preferably, electromagnetic source 310 is disk-like, and is formed of the following layers:
i. a disk-like coil 324, having a proximal side 321 and a distal side 323, with respect to region for treatment 26, and connected to power supply 28, via cables 29;
ii. a backing 322, at distal side 323, on which disk-like coil 324 is arranged;
iii. a conductive membrane 328, at proximal side 321; and
iv. an insulating foil 326, arranged between coil 324 and conductive membrane 328.

Electromagnetic source 310 is thus arranged for generating a collimated pressure pulse 330.

Preferably, disk-like electromagnetic source 310 is arranged in fluid medium 20, with an acoustic lens 312 positioned between source 310 and region for treatment 26. An enclosure 311 and flexible diaphragm 22 contain fluid medium 20 within. When conducting therapeutic treatment, flexible diaphragm 22 is pressed against region for treatment 26, so that pressure pulses propagate through diaphragm 22 to region for treatment 26.

Preferably, acoustic lens 312 is disk-like and is formed of a polymer, or another suitable material. Acoustic lens 312 defines an x-axis passing through its center, and a point of origin O at its center. Acoustic lens 312 is formed of at least two, and preferably more than two acoustic-lens sections, such as first, second and third acoustic-lens sections 314, 316, and 318. These may be substantially or generally focusing lens sections. The shape of each of acoustic-lens sections 314, 316, and 318 determines whether collimated pulse 330, impinging on it, will be directed at a focal point or a general focal zone, and the location of the focal point or zone.

Additionally, given source 310 of collimated pulse 330, impinging on acoustic-lens sections 314, 316, and 318, and given a focal point or zone that is common to acoustic-lens sections 314, 316, and 318, the thickness of each lens section, the lens material, and the distance between the lens section and the common focal point or zone contribute to time differences among pulses reaching the common focal point or zone. Thus, acoustic pulses, originating from source 310, but impinging on different lens sections, will reach the common focal point or zone with phase differences.

Preferably acoustic-lens sections 314, 316, and 318 are designed, preferably by numerical analysis, to have predetermined focal points $F_{314}$, $F_{316}$, and $F_{318}$ which generally coincide at a focal zone F', within region for treatment 26. Alternatively, acoustic-lens sections 314, 316, and 318 are designed, preferably by numerical analysis, as somewhat distorted lens sections, having predetermined general focal zones $F_{314}$, $F_{316}$, and $F_{318}$ rather that focal points. Preferably, focal zones $F_{314}$, $F_{316}$, and $F_{318}$ generally coincide at focal zone F', within region for treatment 26. Alternatively, focal zones $F_{314}$, $F_{316}$, and $F_{318}$ are somewhat displaced from each other, but within region for treatment 26.

Additionally, acoustic-lens sections 314, 316, and 318 are further designed, preferably by numerical analysis, so that pulses directed from them will arrive at focal zone F' with predetermined phase differences of about 0.5-1 microsecond between them.

Preferably, acoustic lens 312 includes at least one cutout section, for example, cutout section A-A, preferably at its center, to allow a portion of collimated primary pulse 330 to pass undisturbed. Thus, at least two acoustic-lens sections of acoustic lens 312 may include at least one cutout section, such as section A-A and at least one additional section such as acoustic lens section 314.

The configuration described in FIG. 7 provides for a collimated primary pulse 330, originating from disk-like source 310, to form a compound of subordinate pulses, which impinge on region for treatment 26 with different phases, as follows:

a. a first pulse 339, which is the center portion of collimated primary pulse 330 passing through cutout section A-A, and is the earliest pulse to reach region for treatment 26, having the shortest path;

ii. a pulse 334, which is a substantially or generally focusing pulse, reflected from lens section 314, toward $F_{314}$ preferably within focal region F', and is preferably the second pulse to reach region for treatment 26, having a path that is only slightly longer than that of pulse 332;

iii. a pulse 336, which is a substantially or generally focusing pulse, reflected from lens section 316, toward $F_{316}$ preferably within focal region F', and is preferably the third pulse to reach region for treatment 26, having a path that is only slightly longer than that of pulse 334; and iv. a pulse 338, which is a substantially or generally focusing pulse, reflected from lens section 318, toward $F_{318}$ preferably within focal region F', and is preferably the fourth pulse to reach region for treatment 26.

In an alternate embodiment, acoustic lens 312 may be formed of cutout section A-A and only one acoustic lens section, such as 314. Alternatively, two, or four, or more than four acoustic lens sections may be used.

In accordance with an alternate embodiment of the present invention, acoustic lens 312 has no cutout section, and is formed of two or more acoustic lens sections.

Figure 8:
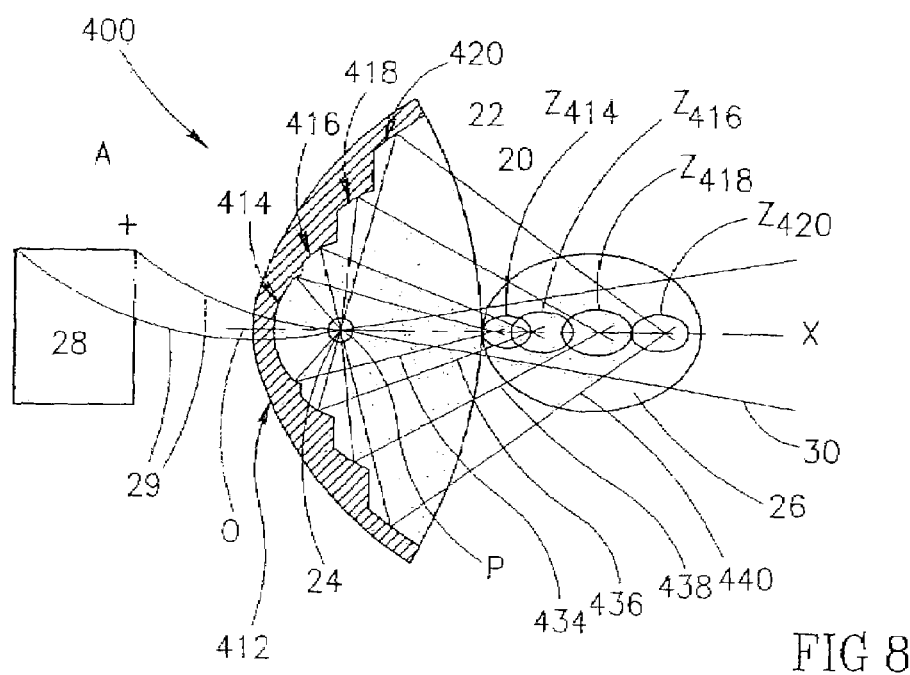
FIG. 8 is a schematic representation of pressure-pulse therapy apparatus, in accordance with a fifth embodiment of the present invention.

Reference is now made to FIG. 8, which schematically illustrates pressure-pulse therapy apparatus 400, in accordance with a fifth embodiment of the present invention. Pressure-pulse apparatus 400 includes a dome-shaped reflector 412, defining an x-axis passing through its center, and a point of origin O at its center. Reflector 412 is formed of a plurality of substantially concentric ring sections, for example, four substantially concentric ring sections 414, 416, 418 and 420, having different curvatures.

Preferably, the curvature of each substantially concentric ring section is determined by a numerical calculation, so as to comply with the following two conditions:

i. a pulse, originating from substantially or generally point source 24 at a point P, and expanding in a radial fashion, will be reflected by the ring section so as to impinge on a predetermined zone $Z_i$, within region for treatment 26, wherein the subscript i denotes a substantially concentric ring section; and ii. a desired time delay, hence a desired phase difference of about 0.5-1 microsecond, will occur between the pulses reflected from adjacent sections.

Alternatively, the curvature of each substantially concentric ring section is determined by a numerical calculation, so that pulses reflected from adjacent sections will all impinge generally on a same, predetermined zone, yet a desired time delay, hence a desired phase difference of about 0.5-1 microsecond, will occur between pulses reflected from adjacent sections.

The configuration seen in FIG. 8 provides for a radically expanding primary pulse 30, originating from substantially or generally point source 24, to form a compound of subordinate pulses, as follows:

i. a pulse 434, reflected from ring section 414 and having the shortest path, will reach region for treatment 26 first, impinging on zone $Z_{414}$;

ii. a pulse 436, reflected from ring section 416, will reach region for treatment 26 second, impinging on zone $Z_{416}$;

iii. a pulse 438, reflected from ring section 418, will reach region for treatment 26 third, impinging on zone $Z_{418}$; and iv. a pulse 440, reflected from ring section 420 and having the longest path, will reach region for treatment 26 last, impinging on zone $Z_{420}$.

Alternatively, zones $Z_{414}$-$Z_{420}$ coincide.

Additionally, a portion of radially expanding primary pulse 30 also impinges upon region for treatment 26, reaching it even before first reflected pulse 434.

In accordance with the present embodiment, reflector 412 includes step changes between adjacent substantially concentric ring sections. Alternatively, reflector 412 is constructed with smooth transitions between adjacent substantially concentric ring sections.

Figure 9A:
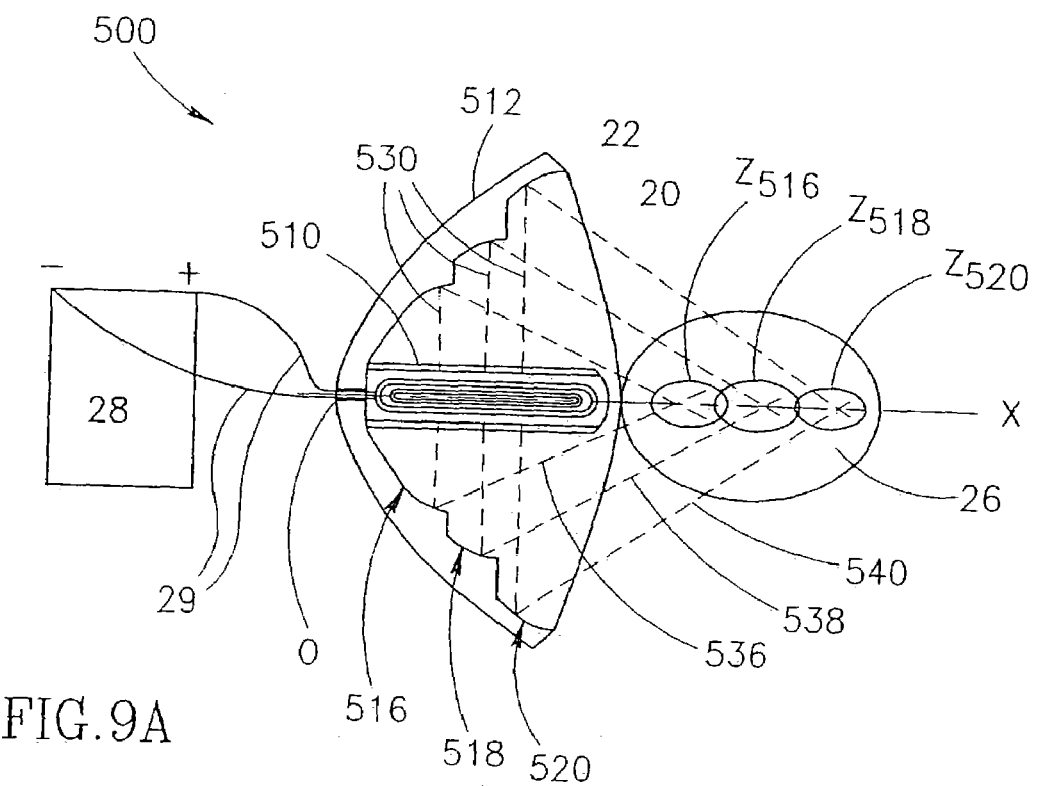
FIGS. 9A-9B together schematically represent pressure-pulse therapy apparatus, in accordance with a sixth embodiment of the present invention.
Figure 9B:
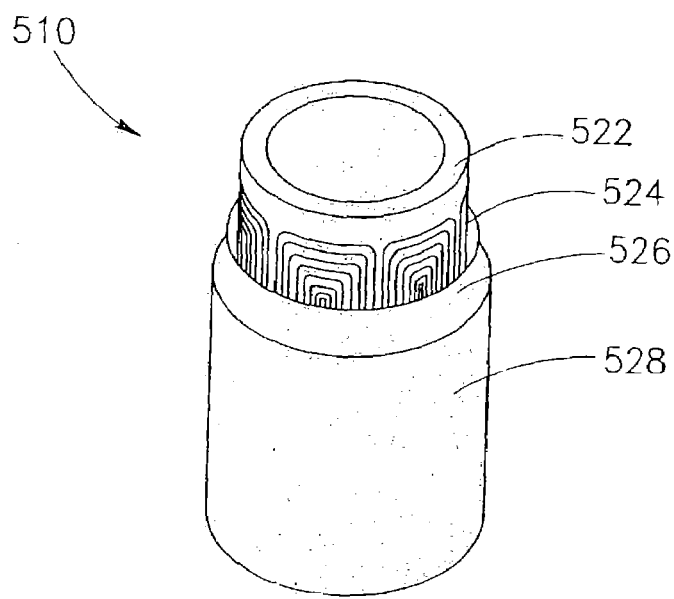

Reference is now made to FIGS. 9A-9B, which together schematically represent pressure-pulse therapy apparatus 500, in accordance with a sixth embodiment of the present invention. Pressure-pulse apparatus 500 includes an electromagnetic source 510, for example, of a type described in European patent EP 0 369 177 B1, incorporated herein by reference. Preferably, electromagnetic source 510 is cylindrical and includes:

i. a cylindrical backing 522;

ii. a coil 524, arranged on an external side of cylindrical backing 522;

iii. an insulating foil 516, external to coil 524; and iv. a conductive membrane 528 external to insulating foil 526.

Pressure-pulse apparatus 500 further includes dome-shaped reflector 512, defining an x-axis passing through its center, and a point of origin O at its center. Dome-shaped, reflector 512 has a vertex at point O and is formed of a plurality of substantially concentric ring sections, for example, three substantially concentric ring sections 516, 518 and 520, having different curvatures. Each substantially concentric ring section is shaped to a curvature, which may be numerically calculated so as to comply with the conditions described hereinabove, in conjunction with FIG. 8.

The configuration of FIGS. 9A and 9B provides for a primary pulse 530, originating from cylindrical source 510, to form a compound of subordinate pulses, as follows:

i. a pulse 536, reflected from ring section 516 and having the shortest path, will reach region for treatment 26 first, impinging on zone $Z_{516}$;
ii. a pulse 538, reflected from ring section 518, will reach region for treatment 26 second, impinging on zone $Z_{518}$; and
iii. a pulse 540, reflected from ring section 520 and having the longest path, will reach region for treatment 26 last, impinging on zone $Z_{520}$.

Alternatively, zones $Z_{516}$, $Z_{518}$, and $Z_{520}$ generally coincide.

In alternate embodiments of the present invention, reflector 512 may be formed of fewer ring sections, or of more ring sections.

In accordance with the present embodiment, reflector 512 includes step changes between adjacent substantially concentric ring sections. Alternatively, reflector 512 is constructed with smooth transitions between adjacent substantially concentric ring sections.

Figure 10:
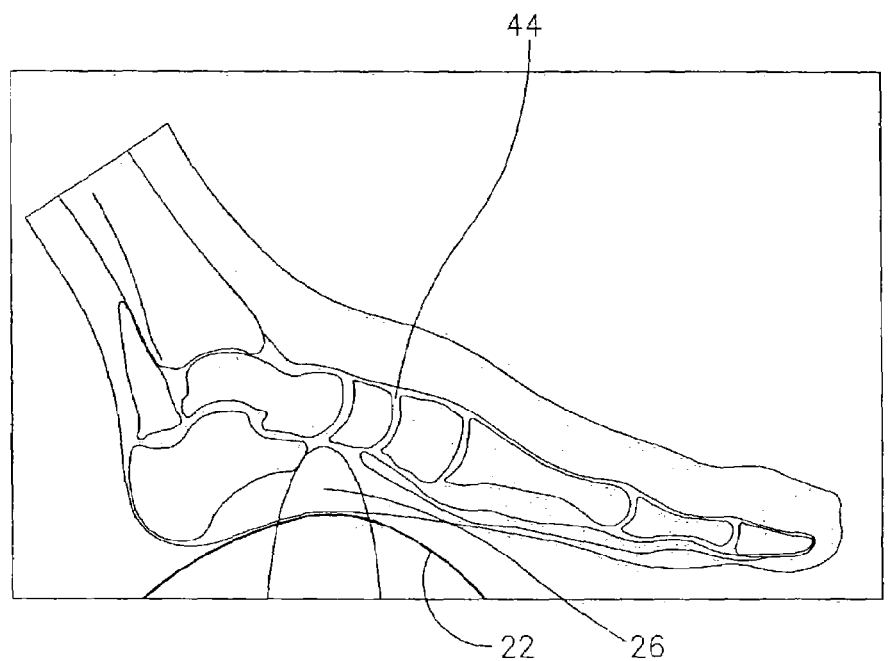
FIG. 10 is a schematic representation of a therapeutic treatment applied to a foot, in accordance with a preferred embodiment of the present invention.

Reference is now made to FIG. 10, which schematically illustrates the application of therapeutic treatment by diaphragm 22 of apparatus 10 to a foot 44, wherein diaphragm 22 presses against surface tissue of foot 44, in accordance with a preferred embodiment of the present invention.

Figure 11A:
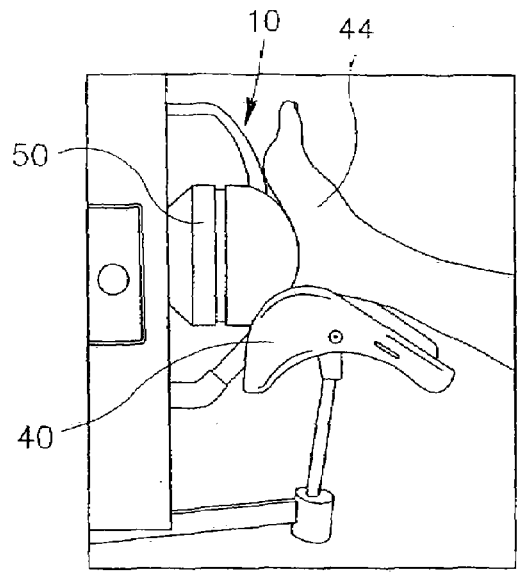
FIGS. 11A-11D are pictorial representations of pressure-pulse therapy apparatus applying therapeutic treatment, in accordance with a preferred embodiment of the present invention.

Reference is now made to FIGS. 11A-11D, which are pictorial representations of apparatus 10 applying therapeutic treatment to different bodily parts, in accordance with some embodiments of the present invention. FIG. 11A illustrates a situation wherein apparatus 10 applies therapeutic treatment to foot 44. A Support fixture 40, such as a foot rest, is used to facilitate the positioning of foot 44 against apparatus 10. Preferably, support fixture 40 is adjustable to support different parts of the body. Preferably, support fixture 40 is removable, so apparatus 10 can be pressed directly against a body when a patient is standing or lying prone. Alternatively, support fixture 40 can be folded in.

Figure 11B:
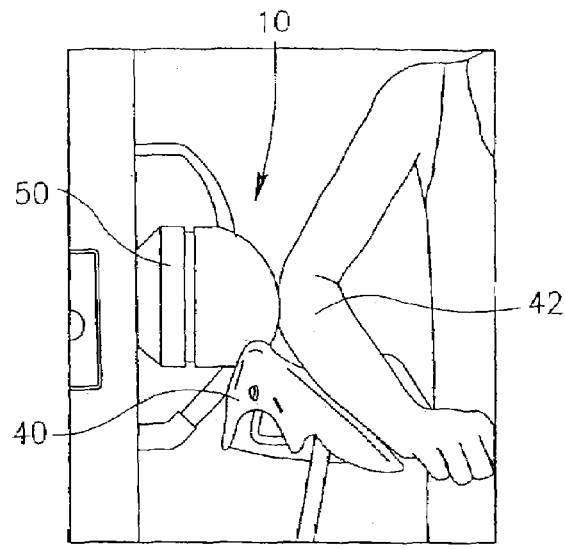

FIG. 11B illustrates a situation wherein apparatus 10 applies therapeutic treatment to an elbow 42, supported by support fixture 40, preferably adjusted for an elbow.

Figure 11C:
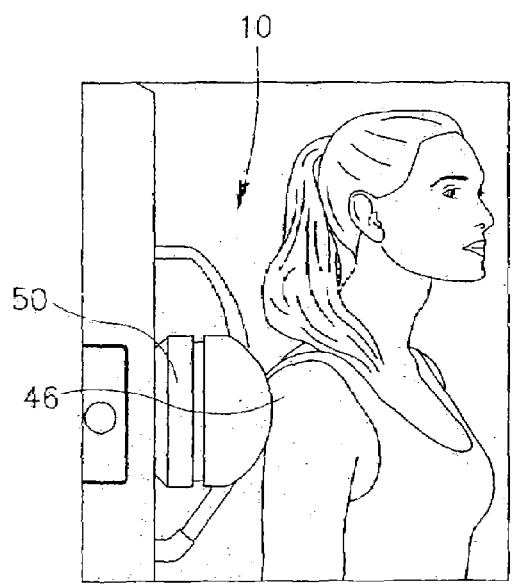

FIG. 11C illustrates a situation wherein apparatus 10 applies therapeutic treatment to a back of a shoulder 46. Preferably, support fixture 40 has been removed or folded in, and apparatus 10 is pressed directly against back of shoulder 46. Preferably apparatus 10 is arranged for traveling along at least one and preferably a plurality of axes, on means of travel 50, such as a gantry or a bellows. Preferably, apparatus 10 is also arranged for tilting in at least one and preferably a plurality of angular directions, also by means of travel 50. Preferably, means of travel 50 provides for easy positioning of apparatus 10 against a body.

Figure 11D:
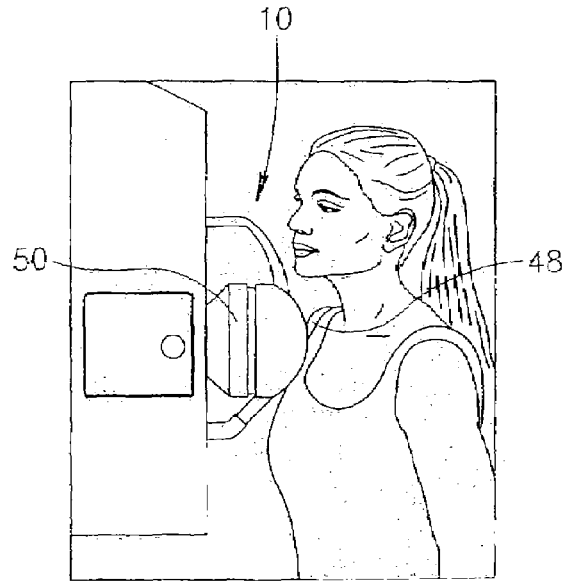

FIG. 11D illustrates a situation wherein apparatus 10 applies therapeutic treatment to a shoulder 48, wherein apparatus 10 is pressed directly against shoulder 48.

In accordance with some embodiments of the present invention, the therapeutic apparatus is used with no accompanying imagine means, since the treatment is regional in nature. Alternatively, x-ray or sonic means are used. Alternatively, another form of imaging means is used.

In accordance with some embodiments of the present invention, the dome-shaped reflector is formed of generally concentric sections. For example, ellipsoid ring sections 16 and 18 (FIG. 1) may be generally concentric with respect to parabolic center section 14, so that distal focal points $F_1 2$ and $F_2 2$ may cluster around the x-axis, slightly off the x-axis. In such a case, ellipsoid ring sections 16 and 18 may be of the same curvature, or of different curvatures.

Preferably, pressure-pulse source 24 is operable to generate primary pressure pulses in the range between 1000 and 6000 bars. Preferably, the therapeutic apparatus is operable to generate, from the primary pressure pulse, subordinate pressure pulses in the range between 5 and 600 bars.

Preferably, power supply unit 28 is as described in U.S. Pat. No. 5,529,572, to Spector, or in PCT publication WO 93/14720, to Spector, both incorporated herein by reference. Alternatively, another suitable power supply unit may be used.

Preferably, the reflector is formed of a material of good acoustic reflection properties, for example, stainless steel, brass or aluminum. Alternatively, another material may be used.

Preferably, the reflector is supported by a mechanical means.

In general the reflector's diameter is between 5 and 40 centimeters, and preferably, between 10 and 25 centimeters.

The present invention may be used in lithotripsy as a non-invasive technique for pulverizing kidney stones and calculi in the bladder and urethra. Additionally, it may be used for dissolving lipids in cells close to the skin and in the pelvic region. Furthermore, it may be used in orthopedic medicine, for example, as a therapeutic means for any of the following:
i. osteoporosis and the inducement of bone growth;
ii. joining of bone fracture, especially, ununion fractures i.e., fractures that have failed to unite and heal;
iii. disintegration of calculi in fibers and joints; and
iv. pain relief in the cases of calcific tendinitis of the shoulder joint, tennis elbow, golf elbow, and plantar fasciitis (with and without heel spur).

It will be appreciated by persons skilled in the art that the scope of the present invention is not limited by what has been specifically shown and described hereinabove, merely by way of example. Rather, the scope of the present invention is limited solely by the claims, which follow.

What is claimed is:

1. Pulsator apparatus for applying pressure-pulses to the outer surface of a body, particularly useful in pressure-pulse therapy, comprising:
   an enclosure open at one end and having a longitudinal axis extending through said open end;
   a pressure-pulse source within said enclosure, at the end thereof opposite to said open end, to generate primary pressure pulses;
   a flexible diaphragm enclosing said open end of the enclosure and adapted to be brought into contact with the surface of the body to receive the pressure pulses;
   a liquid pulse-transmitting medium between said pressure-pulse source and said flexible diaphragm;
   and an acoustical coupling member located with respect to said pressure-pulse source and said liquid pulse-transmitting medium so as to be effective to convert said primary pressure pulses to composite pressure pulses propagated outwardly of said flexible diaphragm in the direction of said longitudinal axis of the enclosure, each of said composite pressure pulses including a non-focussed portion, and at least one focussed portion focussed to a focal point within said non-focussed portion and outwardly of said flexible diaphragm.

2. The pulsator apparatus according to claim 1, wherein said non-focussed portion of each composite pressure pulse is collimated substantially parallel to said longitudinal axis.

3. The pulsator apparatus according to claim 1, wherein said focussed portion of each composite pressure pulse is convergent towards said longitudinal axis.

4. The pulsator apparatus according to claim 1, wherein said focussed portion of each composite pressure pulse is focussed to a focal point on said longitudinal axis of the enclosure, within said non-focussed portion and outwardly of said flexible diaphragm.

5. The pulsator apparatus according to claim 4, wherein each of said composite pressure pulses includes at least a second focussed portion focussed to a second focal point on said longitudinal axis spaced outwardly from said first focal point.

6. The pulsator apparatus according to claim 1, wherein said acoustical coupling member includes a central section for producing said non-focussed portion of each composite pressure pulse, and at least one ring-shaped section around said central section for producing said at least one focussed portion of the composite pressure pulse outwardly of said flexible diaphragm.

7. The pulsator apparatus according to claim 6, wherein said acoustical coupling member is an acoustical reflector having a central section which is substantially parabolic, and wherein said pressure-pulse source is a point source located in the vicinity of the focal point of said substantially parabolic central section of the acoustical reflector so as to produce said non-focussed portion of the composite pressure pulses.

8. The pulsator apparatus according to claim 7, wherein said point-pressure source is carried by a linear extender movable along the longitudinal axis of the enclosure to vary the position of the point pressure source with respect to said acoustical reflector.

9. The pulsator apparatus according to claim 6, wherein said acoustical coupling member is an acoustical lens having a central section formed with a cut-out coaxial to the longitudinal axis of the enclosure, and wherein said pressure-pulse source is a flat-surface source located in alignment with said cut-out of the acoustical lens.

10. The pulsator apparatus according to claim 6, wherein said acoustical, coupling member is an acoustical reflector having a central dome-shaped section; and wherein said pressure-pulse source is a cylindrical-surface source having a longitudinal axis coaxial with the longitudinal axis of said enclosure.

11. The pulsator apparatus according to claim 6, wherein said acoustical coupling member is an acoustical reflector; and said at least one ring-shaped section is substantially ellipsoidal and coaxial with said longitudinal axis of the enclosure.

12. The pulsator apparatus according to claim 6, wherein said pressure-pulse source is a point source, said central section of the reflector is substantially parabolic having a focal point substantially at said point source, and said ring-shaped section of the reflector is substantially ellipsoidal, and has a proximal focal point at or in the vicinity of the focal point of the parabolic reflector section within said enclosure, and a distal focal point outwardly of said enclosure in the vicinity of said flexible diaphragm within said non-focussed portion of the composite pressure pulse.

13. The pulsator apparatus according to claim 6, wherein said acoustical coupling member includes two or more ring-shaped sections all substantially ellipsoidal and coaxial with said longitudinal axis of the enclosure for producing composite pressure pulses having two or more focussed portions focussed to focal points spaced from each other on said longitudinal axis of the enclosure outwardly of said flexible diaphragm.

14. The pulsator apparatus according to claim 13, wherein said pressure pulse source is a cylindrical-surface source having a longitudinal axis coaxial with the longitudinal axis of said enclosure and of said ring-shaped ellipsoidal sections of the acoustical reflector.

15. The pulsator apparatus according to claim 14, wherein said cylindrical pressure pulse source includes a cylindrical core, a plurality of electromagnetic coils in a cylindrical anay around said cylindrical core, and a cylindrical insulating layer over said cylindrical array of coils.

16. The pulsator apparatus according to claim 1, wherein said acoustical coupling member is an acoustical reflector, and includes a central parabolic section coaxial with said longitudinal axis of the enclosure, and at least one ring-shaped ellipsoidal section coaxial with said central parabolic section.

17. The pulsator apparatus according to claim 16, wherein said acoustical reflector includes two or more ellipsoidal sections coaxial with said longitudinal axis of the enclosure for producing composite pressure pulses having two or more focussed portions focussed to focal points spaced from each other on said longitudinal axis of the enclosure outwardly of said flexible diaphragm.

18. The pulsator apparatus according to claim 1, wherein said acoustical coupling member is an acoustical lens, and has a central section formed with a cut-out coaxial with the longitudinal axis of the enclosure, and wherein said pressure-pulse source is a flat-surface source located in alignment with said cut-out of the acoustical lens.

19. The pulsator apparatus according to claim 18, wherein said acoustical lens includes a plurality of two more ring-shaped focusing sections circumscribing said cut-out and coaxial therewith.

20. The pulsator apparatus according to claim 18, wherein said flat pressure-pulse source includes a backing plate having a surface facing said acoustical lens, and a coil supported on said surface of the backing plate with the center of the coil located on the longitudinal axis of the enclosure.

* * * * *